US009387295B1

(12) United States Patent
Mastri et al.

(10) Patent No.: US 9,387,295 B1
(45) Date of Patent: *Jul. 12, 2016

(54) FILTER CARTRIDGE WITH INTERNAL GASEOUS SEAL FOR MULTIMODAL SURGICAL GAS DELIVERY SYSTEM HAVING A SMOKE EVACUATION MODE

(71) Applicant: SurgiQuest, Inc., Milford, CT (US)

(72) Inventors: Dominick Mastri, Bridgeport, CT (US); Ralph Stearns, Bozrah, CT (US); Michael J. Augelli, Prospect, CT (US); Kenneth Blier, Cheshire, CT (US)

(73) Assignee: SurgiQues, Inc., Milford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/609,952

(22) Filed: Jan. 30, 2015

(51) Int. Cl.
*A61M 13/00* (2006.01)
*B01D 46/00* (2006.01)
*A61M 5/165* (2006.01)
*A61B 17/34* (2006.01)
*B01D 51/10* (2006.01)

(52) U.S. Cl.
CPC ............ *A61M 13/003* (2013.01); *A61M 5/165* (2013.01); *A61M 13/006* (2014.02); *B01D 46/0008* (2013.01); *B01D 46/0019* (2013.01); *A61B 17/3474* (2013.01); *A61B 2218/008* (2013.01); *A61M 2210/1021* (2013.01); *B01D 51/10* (2013.01)

(58) Field of Classification Search
CPC . A61M 13/00; A61M 13/003; A61M 13/006; A61M 2210/1021; A61B 17/3474; A61B 2218/008; A61B 17/3421; B01D 46/0008; B01D 46/0019; B01D 51/10
See application file for complete search history.

(56) References Cited

U.S. PATENT DOCUMENTS

| 7,854,724 | B2 | 12/2010 | Stearns et al. | |
| 7,976,598 | B2 * | 7/2011 | Matula | A61M 13/003 210/295 |
| 7,981,072 | B2 * | 7/2011 | Uesugi | A61M 13/003 600/560 |
| 8,088,189 | B2 * | 1/2012 | Matula | A61M 13/003 210/295 |
| 8,795,223 | B2 | 8/2014 | Stearns et al. | |
| 2002/0128603 | A1 * | 9/2002 | Booth | A61B 17/3421 604/164.01 |
| 2005/0015043 | A1 * | 1/2005 | Stubbs | A61B 17/3421 604/26 |
| 2007/0088275 | A1 * | 4/2007 | Stearns | A61B 17/3421 604/164.01 |
| 2007/0163585 | A1 * | 7/2007 | Uesugi | A61M 13/003 128/204.18 |
| 2010/0170208 | A1 * | 7/2010 | Matula | A61M 13/003 55/344 |
| 2010/0185139 | A1 * | 7/2010 | Stearns | A61B 17/3474 604/26 |
| 2012/0138523 | A1 * | 6/2012 | Matula | A61M 13/003 210/232 |
| 2012/0150101 | A1 * | 6/2012 | Stearns | A61B 17/3421 604/24 |
| 2012/0245511 | A1 * | 9/2012 | Stearns | A61B 17/3462 604/26 |
| 2013/0231606 | A1 | 9/2013 | Stearns et al. | |
| 2014/0074015 | A1 * | 3/2014 | Mastri | A61B 17/3474 604/26 |
| 2014/0171855 | A1 | 6/2014 | Mastri et al. | |

* cited by examiner

*Primary Examiner* — Bhisma Mehta
*Assistant Examiner* — Jenna Zhang
(74) *Attorney, Agent, or Firm* — Locke Lord LLP; Scott D. Wofsy (57) ABSTRACT

A system is disclosed for delivering gas during a laparoscopic surgical procedure performed within a patient's abdominal cavity requiring smoke evacuation which includes a gas delivery device having a housing with a port for receiving pressurized insufflating gas from a gas source, a pump assembly for circulating gas throughout the system, and a disposable gas conditioning unit or filter cartridge configured for operative association with the gas delivery device.

34 Claims, 12 Drawing Sheets

FILTER CARTRIDGE WITH INTERNAL GASEOUS SEAL FOR MULTIMODAL SURGICAL GAS DELIVERY SYSTEM HAVING A SMOKE EVACUATION MODE

BACKGROUND OF THE INVENTION

1. Field of the Invention

The subject invention is directed to laparoscopic surgery, and more particularly, to a disposable filter cartridge with an internal gaseous seal for use with a multimodal gas delivery system employed during laparoscopic surgical procedures requiring smoke evacuation from the abdominal cavity of a patient.

2. Description of Related Art

Laparoscopic or "minimally invasive" surgical techniques are becoming commonplace in the performance of procedures such as cholecystectomies, appendectomies, hernia repair and nephrectomies. Benefits of such procedures include reduced trauma to the patient, reduced opportunity for infection, and decreased recovery time. Such procedures within the abdominal (peritoneal) cavity are typically performed through a device known as a trocar or cannula, which facilitates the introduction of laparoscopic instruments into the abdominal cavity of a patient.

Additionally, such procedures commonly involve filling or "insufflating" the abdominal (peritoneal) cavity with a pressurized fluid, such as carbon dioxide, to create what is referred to as a pneumoperitoneum. The insufflation can be carried out by a surgical access device (sometimes referred to as a "cannula" or "trocar") equipped to deliver insufflation fluid, or by a separate insufflation device, such as an insufflation (veress) needle. Introduction of surgical instruments into the pneumoperitoneum without a substantial loss of insufflation gas is desirable, in order to maintain the pneumoperitoneum.

During typical laparoscopic procedures, a surgeon makes three to four small incisions, usually no larger than about twelve millimeters each, which are typically made with the surgical access devices themselves, typically using a separate inserter or obturator placed therein. Following insertion, the inserter is removed, and the trocar allows access for instruments to be inserted into the abdominal cavity. Typical trocars often provide means to insufflate the abdominal cavity, so that the surgeon has an open interior space in which to work.

The trocar must provide a means to maintain the pressure within the cavity by sealing between the trocar and the surgical instrument being used, while still allowing at least a minimum freedom of movement of the surgical instruments. Such instruments can include, for example, scissors, grasping instruments, and occluding instruments, cauterizing units, cameras, light sources and other surgical instruments. Sealing elements or mechanisms are typically provided on trocars to prevent the escape of insufflation gas. Sealing elements or mechanisms typically include a duckbill-type valve made of a relatively pliable material, to seal around an outer surface of surgical instruments passing through the trocar.

Further, in laparoscopic surgery, electrocautery and other techniques (e.g. harmonic scalpels) create smoke and other debris in the surgical cavity, reducing visibility by fogging the view from, and coating surfaces of endoscopes and the like. A variety of surgical smoke evacuation systems are known in the art.

Additionally, SurgiQuest, Inc., Milford, Conn. USA has developed unique surgical access devices that permit ready access to an insufflated surgical cavity without the need for conventional mechanical seals, and it has developed related gas delivery systems for providing sufficient pressure and flow rates to such access devices, as described in whole or in part in U.S. Pat. No. 7,854,724.

The present invention relates to a multimodal gas delivery system and related devices for performing multiple surgical gas delivery functions, including insufflation, smoke evacuation, recirculation and filtration of insufflation fluids and gases. The use of a single multimodal system reduces operating costs by requiring the purchase of only one system while achieving multiple functions, and also thereby reduces the amount of equipment needed in an operating room, thus reducing clutter and allowing space for other necessary equipment.

SUMMARY OF THE INVENTION

The subject invention is directed to a new and useful system for delivering gas during a laparoscopic surgical procedure performed within a patient's abdominal cavity. The system includes, among other things, a gas delivery device having a housing with a port for receiving insufflating gas from a gas source. The gas delivery device includes a pump assembly for circulating pressurized gas throughout the system. The system further includes a disposable gas conditioning unit or cartridge configured for operative association with the gas delivery device.

The gas conditioning system includes a first internal flow path for receiving pressurized gas delivered from the pump, a second internal flow path for delivering insufflating gas to the abdominal cavity at a desired flow rate and pressure and for facilitating periodic static pressure measurements from the abdominal cavity, and a third internal flow path for returning pressurized gas to the pump.

In accordance with a preferred embodiment of the subject invention, the first internal flow path includes a nozzle assembly configured to accelerate the pressurized gas delivered by the pump and thereby generate a continuous pressure barrier contained within the gas conditioning unit. The pressure barrier or working zone that inhibits the egress of insufflating gas from the abdominal cavity and functions to maintain a stable pneumoperitoneum during a surgical procedure.

The gas conditioning unit includes a generally cylindrical housing having an inlet end and an opposed outlet end. The gas delivery device includes an engagement port for detachably receiving the gas conditioning unit. The outlet end of the gas conditioning unit includes an outlet cover having a first outlet port corresponding to the first internal flow path, a second outlet port corresponding to the second internal flow path and a third outlet port corresponding to the third internal flow path.

The inlet end of the gas conditioning unit includes an inlet cover having a first inlet port corresponding to the first internal flow path which communicates with a first conduit, a second inlet port corresponding to the second internal flow path which communicates with a second conduit and a third inlet port corresponding to the third internal flow path which communicates with a third conduit.

The housing of the gas conditioning unit includes a pressure chamber located within the first internal flow path and communicating with the first outlet. The housing of the gas conditioning unit further includes a central nozzle chamber having a cylindrical wall supporting the nozzle assembly. The central nozzle chamber communicates with the pressure chamber through an internal delivery port.

The nozzle assembly includes a cylindrical jet set having a pair of axially spaced apart outer sealing rings for sealingly isolating the nozzle assembly within the central nozzle chamber. The central nozzle chamber includes a plurality of circumferentially disposed spaced apart axial fins or vanes located distal to the cylindrical jet set of the nozzle assembly for directing gas flow away from the working zone. The central nozzle chamber communicates with a breathing tube proximal to the cylindrical jet set that is open to atmosphere to facilitate entrainment of air into the gas delivery system under certain operating conditions.

A first filter element is disposed within the pressure chamber for filtering pressurized gas delivered from the pump. The housing of the gas conditioning unit includes a diverter plate which interacts with the outlet cover to define a conditioning cavity disposed in the second internal flow path and configured to support a second filter element for filtering insufflating gas from the gas source.

The housing of the gas conditioning unit also includes a vacuum chamber located within the third internal flow path. The vacuum chamber communicates with the nozzle chamber through a plurality of gas transfer ports to permit spent gas from the nozzle assembly to return to the pump for repressurization and circulation. A third filter element is disposed within the vacuum chamber for filtering gas returning to the pump from the patient's abdominal cavity.

The housing of the gas conditioning unit further includes a reservoir chamber located within the third internal flow path, downstream from and in fluid communication with the vacuum chamber through a fluid transfer port. The reservoir chamber will accommodate fluid and debris drawn into the housing of the gas conditioning unit by the suction of the pump. A fluid level sensor is arranged within the reservoir for detecting a predetermined fluid level therein, and alarm set points are associated with these sensors.

The first conduit includes a fitting for communicating with a first surgical access port, and the first surgical access port includes a mechanical valve or seal associated with a central lumen thereof for accommodating the introduction of surgical instruments into the abdominal cavity. The second conduit includes a fitting for communicating with a second surgical access port responsible for insufflation of and pressure measurement from the abdominal cavity. The third conduit includes a fitting for communicating with a third surgical access port responsible for smoke evacuation from the abdominal cavity.

The subject invention is also directed to a gas conditioning unit for use with gas delivery device during a laparoscopic surgical procedure performed within a patient's abdominal cavity. The unit includes a housing having an inlet end configured for engagement with the gas delivery device and an opposed outlet end, a first filtered flow path within the housing for receiving pressurized gas from a pump within the gas delivery device, a second filtered flow path within the housing for delivering insufflating gas to the abdominal cavity and for periodically sensing static pressure through a second conduit connected to the outlet end of the housing, and a third filtered flow path for returning pressurized gas to the pump.

Preferably, the first filtered flow path includes an annular nozzle assembly with a plurality of jets that are dimensioned and configured to accelerate the pressurized gas delivered by the pump and thereby generate a continuous pressure barrier or working zone contained within the gas conditioning unit that inhibits egress of insufflation gas from the abdominal cavity, while maintaining a stable pneumoperitoneum.

The outlet end of the conditioning unit or cartridge includes an outlet cover having a first outlet port corresponding to the first filtered flow path, a second outlet port corresponding to the second filtered flow path and a third outlet port corresponding to the third filtered flow path.

The inlet end of the gas conditioning unit includes an inlet cover having a first inlet port corresponding to the first filtered flow path which communicates with the first conduit, a second inlet port corresponding to the second filtered flow path which communicates with the second conduit and a third inlet port corresponding to the third filtered flow path which communicates with the third conduit. The housing of the gas conditioning unit includes a pressure chamber located within the first flow path and communicating with the first outlet.

The housing of the gas conditioning unit also includes a central nozzle chamber having a cylindrical wall supporting the annular nozzle assembly. The central nozzle chamber communicates with the pressure chamber through an internal delivery port. The annular nozzle assembly includes a cylindrical jet set having a pair of axially spaced apart outer sealing rings for sealingly isolating the nozzle assembly within the central nozzle chamber. The central nozzle chamber includes a plurality of circumferentially disposed spaced apart axial fins distal to the cylindrical jet set for directing gas flow. The central nozzle chamber communicates with a breathing tube proximal to the cylindrical jet set that is open to atmosphere for air entrainment.

A first filter element is disposed within the pressure chamber for filtering pressurized gas from the pump. The housing of the gas conditioning unit includes a diverter plate which interacts with the outlet cover to define a conditioning cavity disposed in the second filtered flow path and configured to support a second filter element for filtering insufflation gas from the gas source.

The housing of the gas conditioning unit also includes a vacuum chamber located within the third filtered gas path. The vacuum chamber communicates with the nozzle chamber through a plurality of gas transfer ports to permit spent gas from the nozzle assembly to return to the pump for repressurization and circulation. A third filter element is disposed within the vacuum chamber for filtering gas returning to the pump from the patient's abdominal cavity.

The housing of the gas conditioning unit further includes a reservoir chamber located within the third filtered flow path, downstream from and in fluid communication with the vacuum chamber through a fluid transfer port, for accommodating any fluid or debris drawn into the housing of the gas conditioning unit by the suction of the pump. A fluid level sensor is arranged within the reservoir for detecting a predetermined fluid level therein. An alarm is operatively associated with these sensors.

The first conduit includes a fitting for communicating with a first surgical access port, and the first surgical access port includes a mechanical valve associated with a central lumen thereof for accommodating the introduction of surgical instruments into the abdominal cavity. The second conduit includes a fitting for communicating with a second surgical access port responsible for insufflation and pressure measurement of the abdominal cavity. The third conduit includes a fitting for communicating with a third surgical access port responsible for smoke evacuation from the abdominal cavity.

These and other features of the surgical gas delivery system and the gas conditioning device of the subject invention and the manner in which both are manufactured and employed will become more readily apparent to those having ordinary skill in the art from the following enabling description of the preferred embodiments of the subject invention taken in conjunction with the several drawings described below.

BRIEF DESCRIPTION OF THE DRAWINGS

So that those skilled in the art to which the subject invention appertains will readily understand how to make and use the gas delivery system of the subject invention without undue experimentation, preferred embodiments thereof will be described in detail herein below with reference to certain figures, wherein.

DETAILED DESCRIPTION OF PREFERRED EMBODIMENTS

Figure 1:
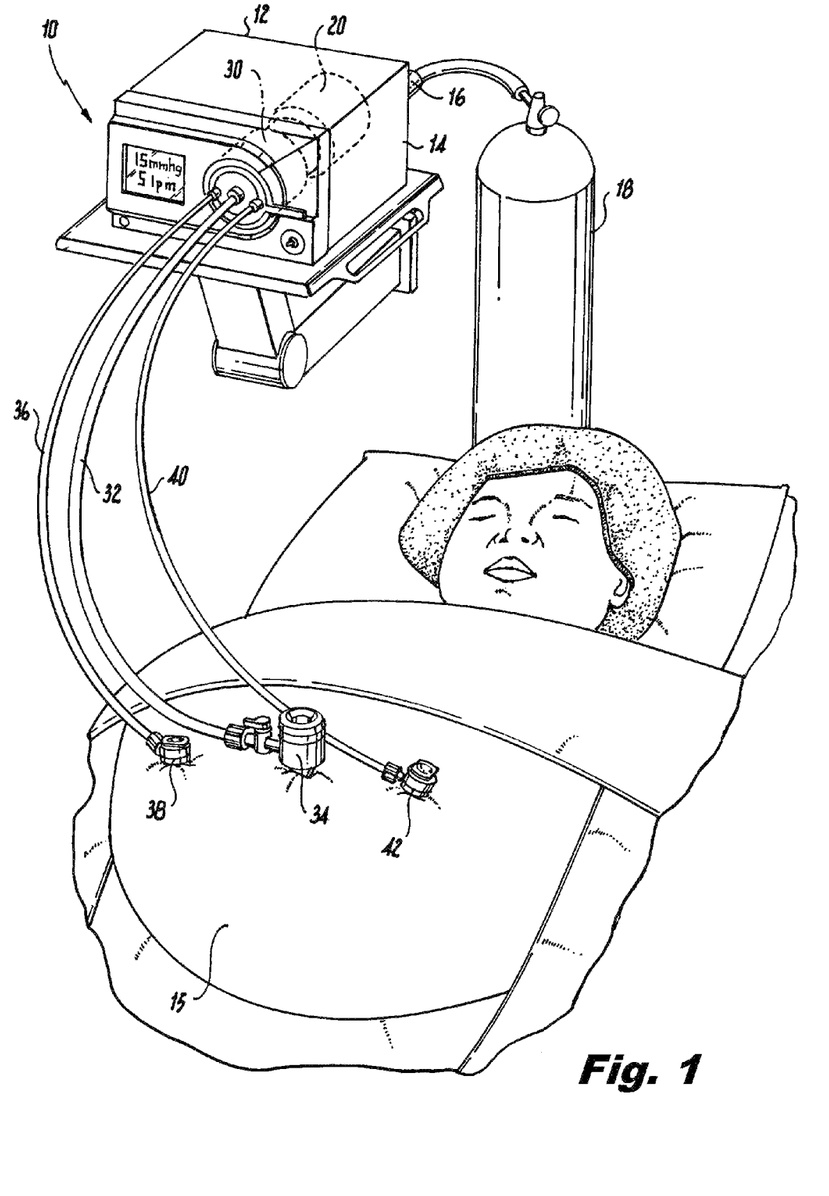
FIG. 1 is an illustration of the operating environment in which the gas delivery system of the subject invention is employed during a laparoscopic surgical procedure, which includes, among other things, a gas delivery device having a housing with a port for receiving insufflation gas from a gas source, a pump for circulating pressurized gas and a disposable gas conditioning unit.
Figure 2:
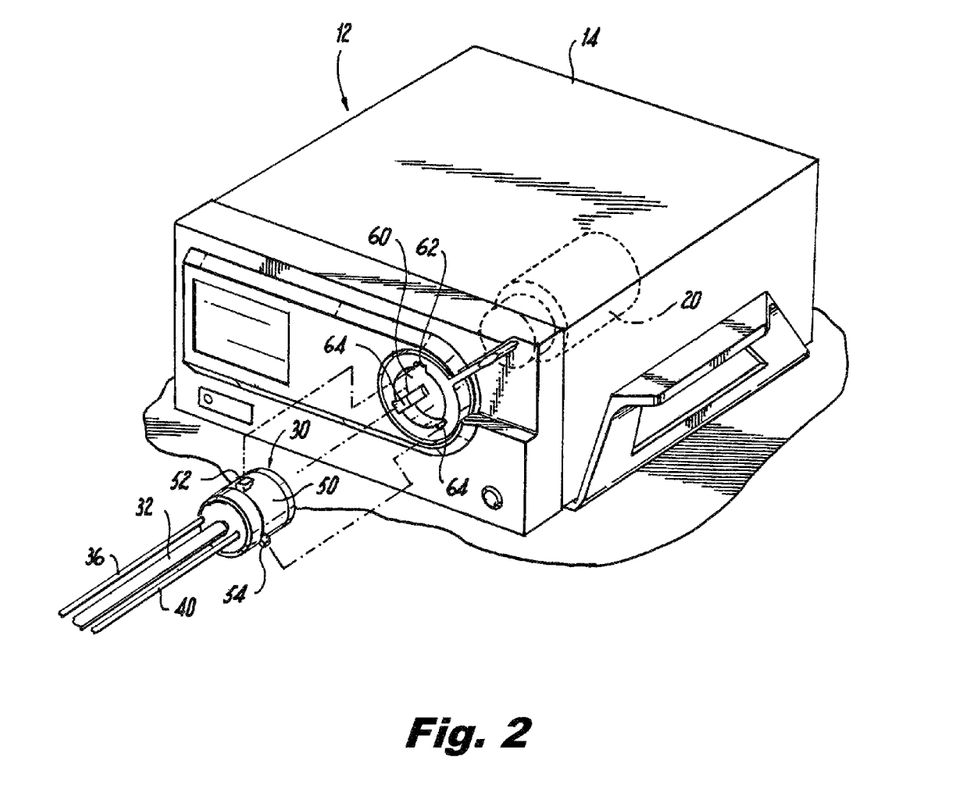
FIG. 2 is a perspective view of the gas delivery device and separate gas conditioning unit illustrated in FIG. 1.

Referring now to the drawings wherein like reference numerals identify similar structural features or aspects of the subject invention, there is illustrated in FIGS. 1 and 2, a new and useful system for delivering and circulating medical gas (e.g., carbon dioxide) during a laparoscopic surgical procedure performed within a patient's abdominal cavity that involves the evacuation of smoke generated from an electrocautery device or other instrument (e.g., harmonic scalpels), which would otherwise reduce visibility within the cavity by fogging the view from, and coating surfaces of endoscopes and the like.

The gas delivery system, which is designated generally by reference numeral 10 includes, among other things, a gas delivery device 12 having a housing 14 with a rear connector or port 16 for receiving pressurized insufflation gas from a gas source 18. As shown, the gas source 18 is a portable supply canister. However, it is envisioned that the medical or insufflating gas could be supplied from another source, including for example, a remote storage tank (e.g., house gas) as is well known in the art. A pump assembly 20 is enclosed within the housing 14 of delivery device 12 for circulating pressurized gas throughout the system 10 to maintain a stable pneumoperitoneum during a surgical procedure.

A graphical user interface 25 with associated control circuitry is provided within the housing 14 of gas delivery device 12 for controlling the operation of the pump assembly 20, as well as the delivery of insufflating gas from supply source 18. The interface and associated circuitry enables a user to readily adjust flow rates and supply pressures relating to the delivery, circulation and recirculation of gas and fluid throughout the system.

The gas delivery system 10 further includes a separate and preferably disposable gas conditioning unit 30, which is dimensioned and configured for operative association with the gas delivery device 12. As described in more detail below, the gas conditioning unit 30 is constructed in such a manner so that a continuous gaseous pressure barrier is generated within the housing of the unit itself, remote from the patient. This gaseous pressure barrier or working zone prevents the egress of insufflation gas from the abdominal cavity of the patient while maintaining a stable pneumoperitoneum within the abdominal cavity. This feature differs from the multi-modal gas delivery systems disclosed in commonly assigned U.S. Pat. No. 7,854,724, wherein the gaseous pressure barrier is generated within the housing of a specialized trocar at the surgical site.

The gas conditioning unit 30 includes a number of internal flow paths configured to facilitate the periodic delivery of insufflating gas, as well as the continuous circulation and recirculation of pressurized gas. In particular, a first internal flow path (i.e., the pressure path shown in FIG. 11) is provided for receiving pressurized gas from the pump assembly 20 of the gas delivery device 12. The first internal flow path is associated with a first conduit 32 that is connected to a first surgical access device or trocar 34. The trocar 34 is the primary path for introducing surgical instrumentation into the abdominal cavity during a surgical procedure, and it has a mechanical seal installed therein. The pressurized gas is used to create a pressure barrier within the gas conditioning unit 30 that prevents the egress of gas from the abdominal cavity by way of conduit 32. In doing so, it also maintains a stable pneumoperitoneum within the abdominal cavity of the patient 15.

The gas conditioning unit 30 further includes a second internal flow path (i.e., the sense/insufflation path shown in FIG. 10) for delivering insufflating gas from the gas delivery device 12 to the abdominal cavity of the patient 15 and for facilitating periodic static pressure measurements from the abdominal cavity by way of a second conduit 36 connected to a second surgical access device or cannula 38. The duration of the insufflation interval between pressure measurements can vary, depending upon the patient and the operating environment. This flow and stop methodology for obtaining static pressure measurements from the abdominal cavity is well known in the art.

The gas conditioning unit 30 also includes a third internal flow path (i.e., the vacuum path shown in FIG. 13) for returning pressurized gas to the pump assembly 20 of the gas delivery device 12 by way of a third conduit 40 connected to a second surgical access device or cannula 42. The gas returned to the pump assembly 20 comes from two locations or sources. This includes the pressurized gas that was used to create the pressure barrier within the conditioning unit 30 and gas from within the abdominal cavity of the patient 15 that may be carrying smoke and debris resulting from an electrocautery procedure or the like.

Figure 3:
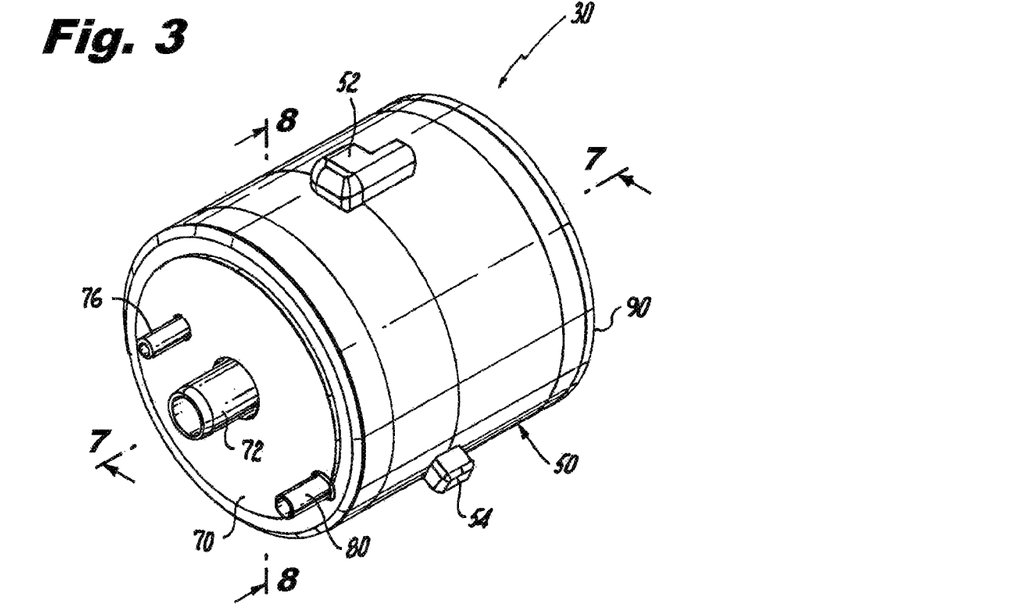
FIG. 3 is a perspective view of the gas conditioning unit of the subject invention as viewed from the front end of the unit, illustrating the three conduits extending therefrom.
Figure 4:
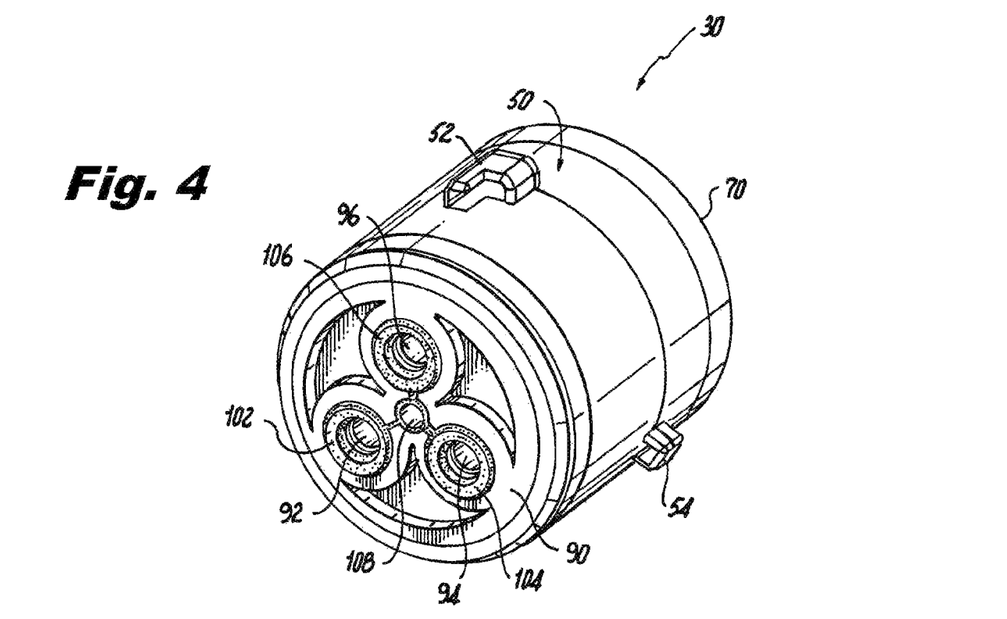
FIG. 4 is a perspective view of the gas conditioning unit of the subject invention as viewed from the rear end of unit, illustrating the three ports thereof.

With continuing reference to FIG. 2, the gas conditioning unit 30 is adapted and configured for ready installation into and removal from the housing 14 of gas delivery device 12 by way of a interfitting lug arrangement. More particularly, as best seen in FIGS. 3 and 4, the generally cylindrical housing 50 of gas conditioning unit 30 includes a plurality of circumferentially spaced apart engagement lugs, including an L-shaped lug 52 and a square-shaped lug 54. A third lug 56 can be seen in FIG. 8. The three engagement lugs 52, 54 and 56 are dimensioned and configured to interact with correspondingly shaped and positioned recesses 62, 64 and 66 defined in the periphery of the cartridge engagement port 60 formed in the front panel of housing 14, as shown in FIG. 2.

With continuing reference to FIGS. 3 and 4, the housing 50 of gas conditioning unit 30 includes a front end cap or inlet cover 70 and a rear end cap or outer cover 90. The front end cap 70 has three conduit connection tubes associated therewith. These include a first or central conduit connection tube 72 that extends through an aperture 75 in the front end cap 70 and is operatively associated with the first conduit 32, shown in FIGS. 1 and 2. Front end cap 70 also includes a second conduit connection tube 76 operatively associated with the second conduit 36 and a third conduit connection tube 80 operatively associated with the third conduit 40, which are also shown in FIGS. 1 and 2.

The rear end cap 90 includes three outlet ports, each having an associated sealing ring. The first outlet port 92 communicates with the first internal flow path (i.e., the pressure path shown in FIG. 11) and ultimately with tube 72. The second outlet port 94 communicates with the second internal flow path (i.e., the sense/insufflation path shown in FIG. 10) and ultimately with tube 80. The third outlet port 96 communicates with the third internal flow path (i.e., the vacuum path shown in FIG. 13) and ultimately with tube 96.

The first outlet port 92 includes a first O-ring seal 102, the second outlet port 94 includes a second O-ring seal 104 and the third outlet port 96 includes a third O-ring seal 106. The three O-rings seals 102, 104 and 106 are seated and arranged in a co-planar manner on the rear end cap 90 to cooperate with corresponding features within the cartridge engagement port 60 in the front panel of housing 14.

A similar co-planar arrangement of O-ring seals is disclosed in commonly assigned U.S. Patent Application Publication 2012/0138523, which is incorporated herein by reference in its entirety. In addition, the rear end cap 90 includes a central exhaust port 108, which permits the entrainment of air into the recirculation flow under certain operating conditions. This will be described in more detail hereinbelow.

Figures 5, 6:
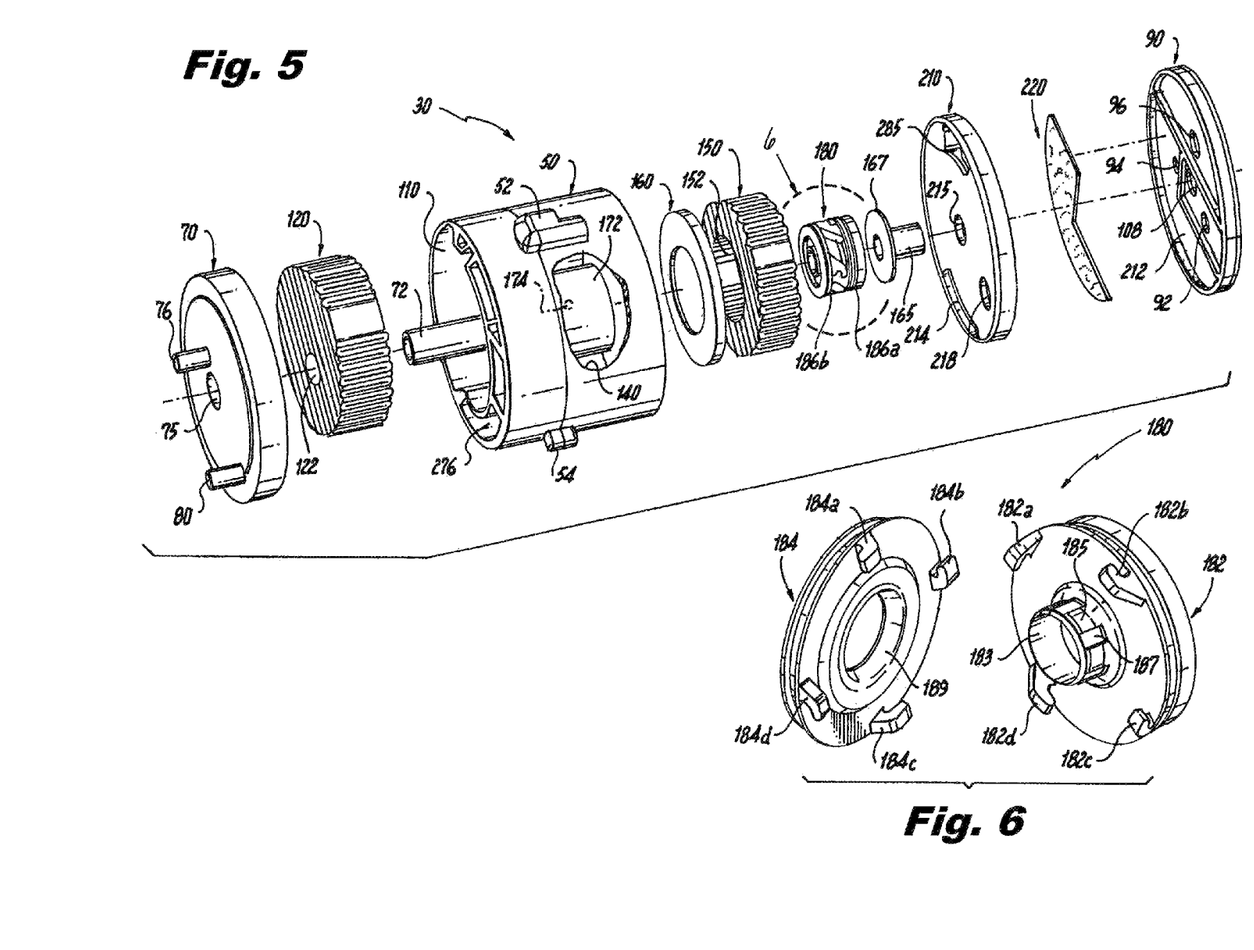
FIG. 5 is an exploded perspective view of the gas conditioning unit of the subject invention, with parts separated for ease of illustration.
FIG. 6 is an exploded perspective view of the annular jet rings which form the internal nozzle assembly of the gas conditioning unit shown in FIG. 5.

Referring now to FIG. 5, there is illustrated the gas conditioning unit 30 with each of the components parts thereof separated from the cylindrical housing 50 for ease of illustration. Also shown are certain internal features of the housing 50 of conditioning unit 30. Starting there, the housing 50 includes several internal cavities for supporting components and/or defining gas/fluid flow passages. At the front end of housing 50, there is a vacuum chamber 110, which is located within the third internal flow path (i.e., the vacuum path shown in FIG. 13).

Figure 7:
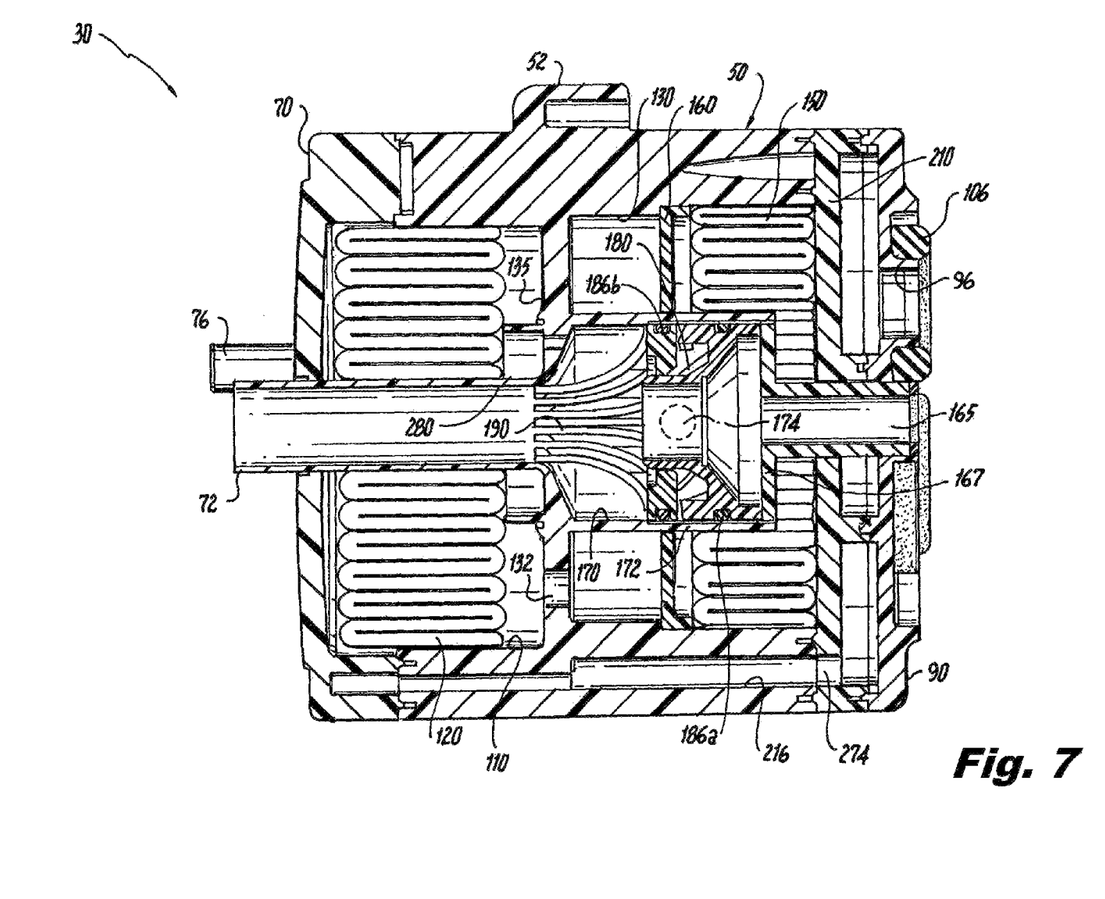
FIG. 7 is a cross-sectional perspective view of the gas conditioning unit of the subject invention taken along line 7-7 of FIG. 3, illustrating the location of the filter elements within the housing of the gas conditioning unit.

The vacuum chamber 110 is dimensioned and configured to support a cylindrical pleated filter element 120 (see also FIG. 7). The pleated filter element 120 is preferably made from a porous non-woven or melt-blown filter media fabricated from a plastic material such as polypropylene or the like. Filter element 120 has an offset bore 122 to accommodate the passage of the central conduit connection tube 72 therethrough, when the unit 30 is fully assembled.

Figure 9:
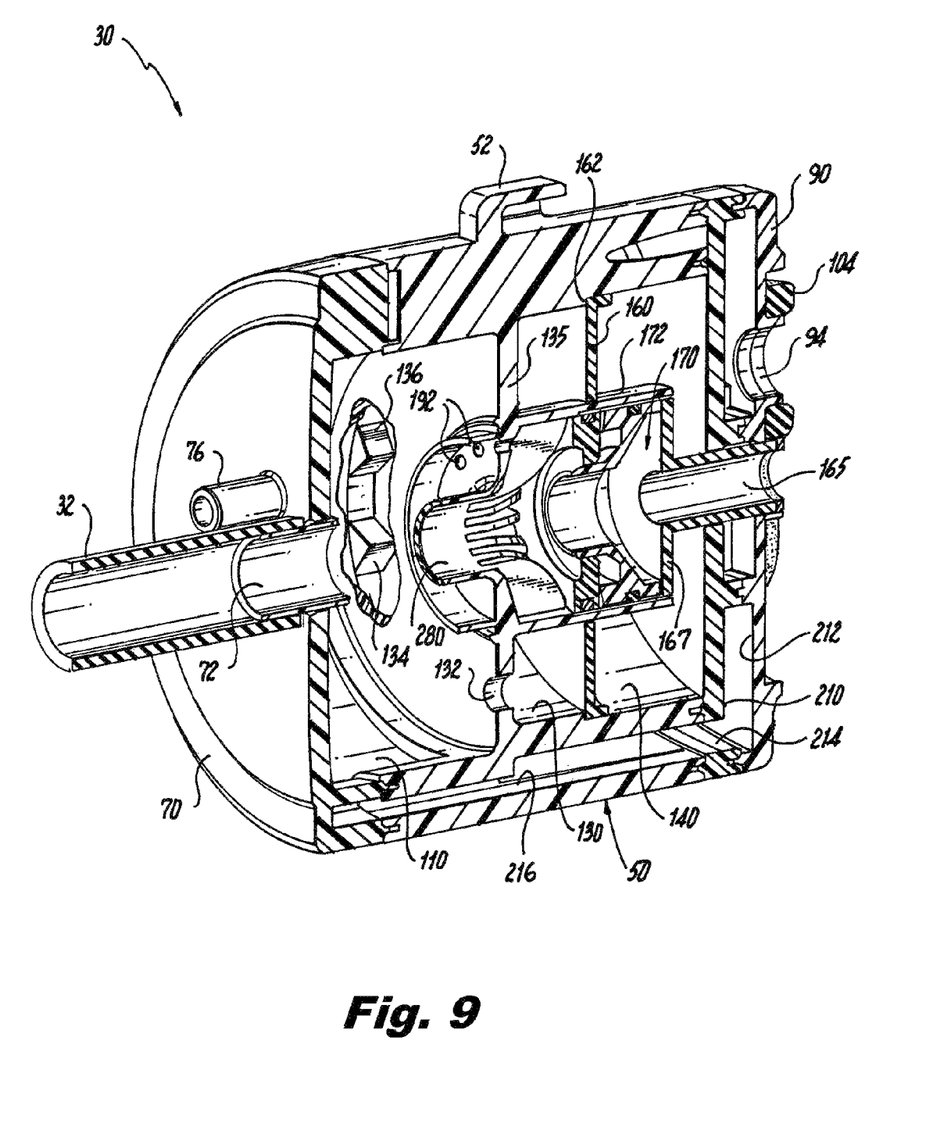
FIG. 9 is a cross-sectional view of the gas conditioning unit of the subject invention, with a wall broken away to show the liquid level sensing prisms in the reservoir.

As best seen in FIGS. 7 and 9, the housing 50 of gas conditioning unit 30 further includes a reservoir chamber 130, which is also located within the third internal flow path, downstream from and in fluid communication with the vacuum chamber 110. More particularly, the reservoir chamber 130 communicates with the vacuum chamber 110 through a fluid transfer port 132 formed in the internal wall 135 of housing 50. Any fluid or debris drawn into the housing 50 of the gas conditioning 30 unit by the suction of pump 20 in gas delivery device 12 accumulates first within the vacuum chamber 110 until it reaches the level of the transfer port 132, whereupon such fluid enters into the reservoir chamber 130.

Referring to FIG. 9, prism shaped fluid level sensors 134 and 136 are arranged within the reservoir chamber 130 for detecting a predetermined fluid level therein. The structure and function of the fluid level sensors 134, 136, and the alarm set points and circuity associated therewith is described in greater detail in commonly assigned U.S. Patent Application Publication 2013/0231606, the disclosure of which is herein incorporated by reference in its entirety.

Figure 11:
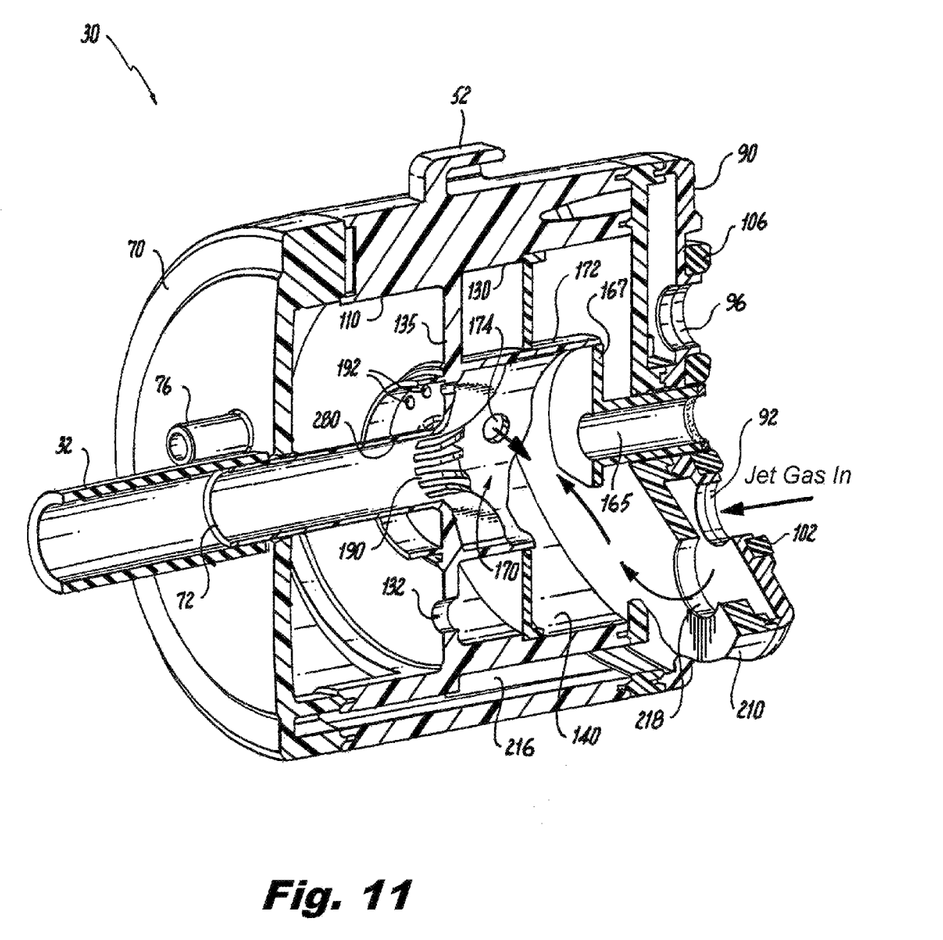
FIG. 11 is a cross-sectional view of the gas conditioning unit of the subject invention with a wall broken away to illustrate the pressure path layout within the housing of the unit.

With continuing reference to FIG. 5 in conjunction with FIGS. 7 and 9, the housing 50 of gas conditioning unit 30 further includes a pressure chamber 140 located within the first internal flow path (i.e., the pressure path shown in FIG. 11). Pressure chamber 140 is dimensioned and configured to support a cylindrical pleated filter element 150 (see also FIG. 7). Pleated filter element 150 is preferably made from a porous non-woven or melt-blown filter media fabricated from a plastic material such as polypropylene or the like.

Filter element 150 has a central bore 152 to accommodate a cylindrical breathing tube 165. Breathing tube 165 communicates with the central breathing port 108 in the rear end cap 90 to facilitate the entrainment of ambient air into the system under certain operating conditions. As best seen in FIGS. 5 and 7, an annular barrier wall 160 separates and fluidly isolates the reservoir chamber 130 from the pressure chamber 140. The barrier wall 160 is seated on an annular ledge 162 formed in the inner wall of the housing 50.

The housing 50 of gas conditioning unit 30 also includes a central nozzle chamber 170 defined primarily by a cylindrical wall 172, which is surrounded by pleated filter 150. The central nozzle chamber 170 communicates with the pressure chamber 140 through an internal delivery port 174 (see FIGS. 5 and 11). The central nozzle chamber 170 supports a two-part annular nozzle assembly 180, which is shown in a separated condition in FIG. 6. The annular nozzle assembly 180 is described in greater detail in commonly assigned U.S. Pat. No. 8,795,223, which is herein incorporated by reference in its entirety.

In general, the annular nozzle assembly 180 includes upper and lower ring jet components 182 and 184, which are connected to one another by a set of circumferentially spaced apart cooperating lugs 182a-182d and 184a-184d. The upper ring jet component 182 includes a central tubular portion 183 having a set of circumferentially spaced apart recessed areas 185 forming a set of spaced apart land areas 187. The lower ring jet component 184 includes a continuous seating surface 189 for intimately receiving the tubular portion 183 of upper ring jet component 182.

Figure 12:
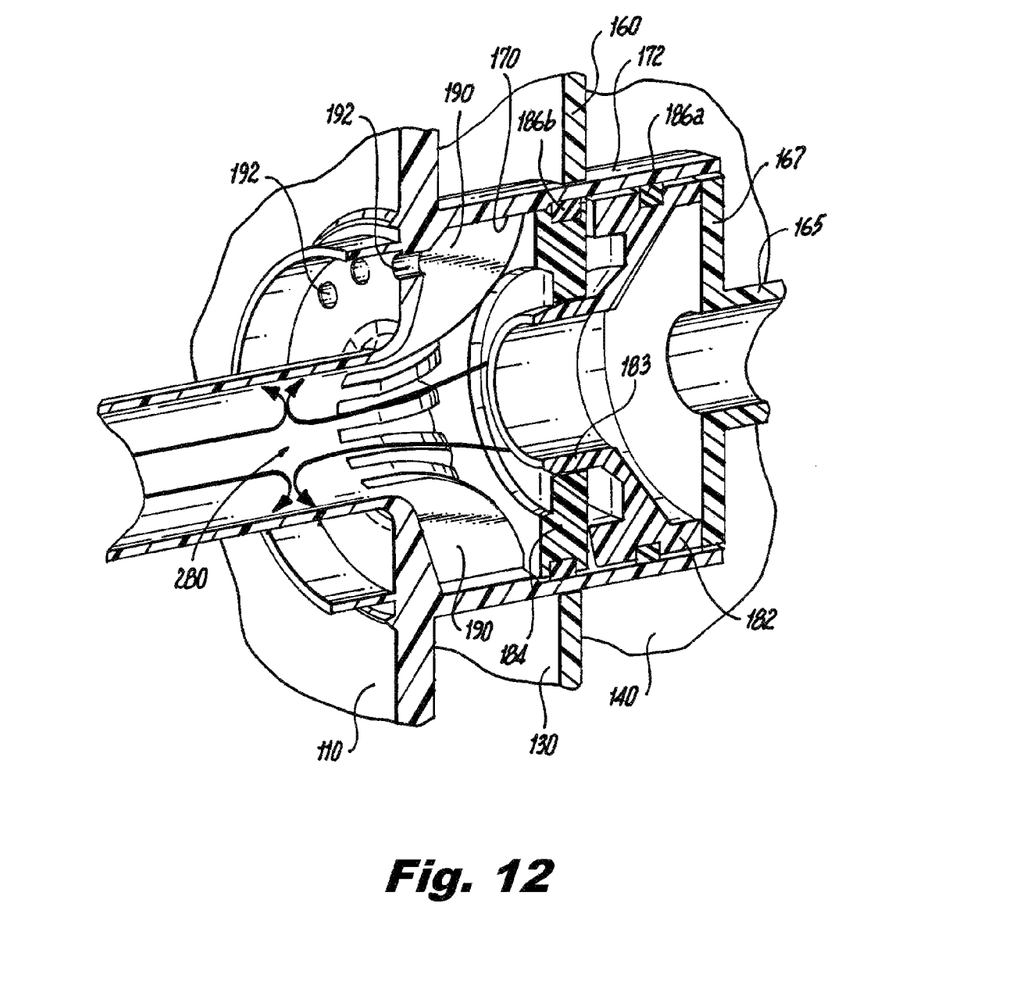
FIG. 12 is a localized cross-sectional view of the central nozzle chamber within the housing, where the internal pressure barrier or working zone is formed by the nozzle assembly, remote from the surgical site.

When the two ring jet components 182, 184 are interfit together, an annular nozzle is formed between the land areas 187 of the tubular portion 183 and the continuous seating surface 189. When pressurized air is delivered from the pressure chamber 140, through the delivery port 174, into the nozzle chamber 170, and then through the nozzle 180 formed by the intimate engagement of the tubular portion 183 and the continuous seating surface 189, a pressure barrier or working zone is created within the housing 50 of conditioning unit 30 to prevent the egress of insufflation gas from the abdominal cavity of a patient by way of conduit 32. This is best seen in FIG. 12.

The annular nozzle assembly 180 further includes a pair of axially spaced apart outer sealing rings 186a, 186b for sealingly isolating the nozzle assembly 180 within the central nozzle chamber 170, as best seen in FIG. 7. The central nozzle chamber 170 of housing 50 includes a plurality of circumferentially disposed spaced apart axial vanes or fins 190 located distal to the cylindrical jet set 182, 184. The vanes 190 are adapted and configured to direct the flow of spent gas (i.e., pressurized gas that has lost its momentum after being delivered from the jet set nozzle assembly 180) away from the working zone.

The central nozzle chamber 170 communicates with the breathing tube 165, which is located proximal to the nozzle assembly 180. The breathing tube 165 is open to atmosphere and permits the entrainment of air into the recirculation flow of the gas delivery system under certain operating conditions. The breathing tube 165 includes a base portion 167 that forms an end cap for the nozzle chamber 170.

Figure 8:
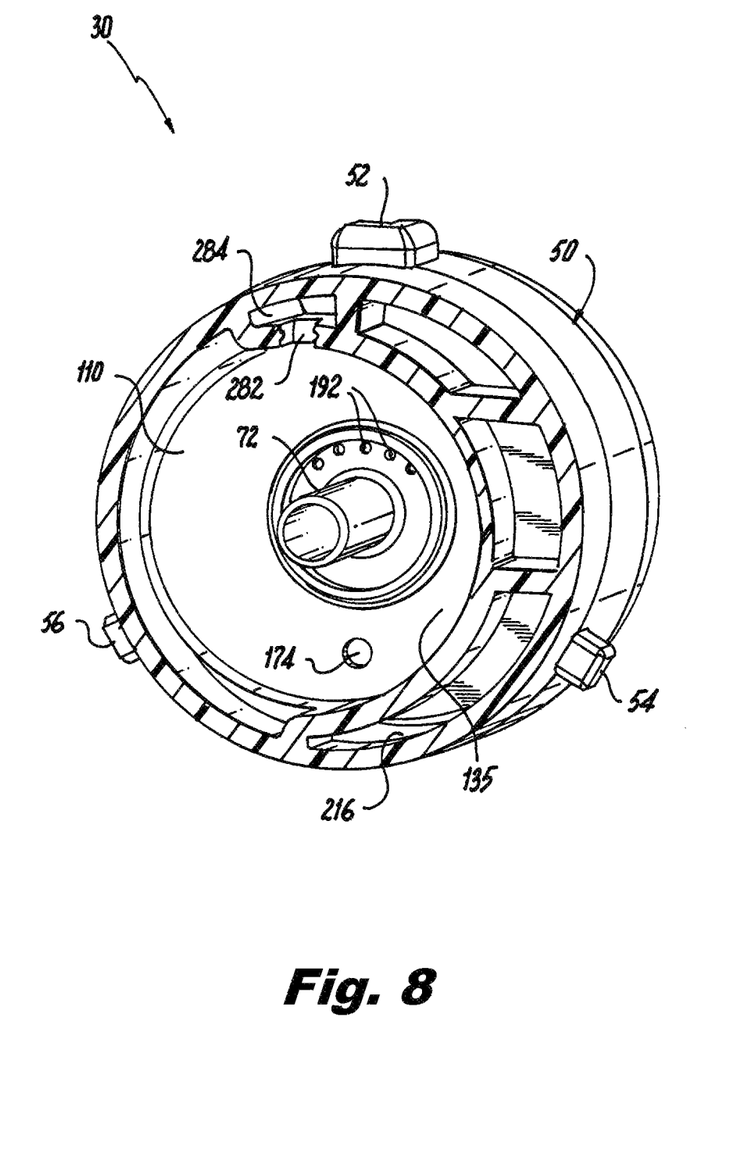
FIG. 8 is a cross-sectional perspective view of the gas conditioning unit of the subject invention, taken along line 8-8 of FIG. 3, illustrating the internal features of the vacuum chamber within the housing of the unit.

Referring to FIGS. 8 and 9, the vacuum chamber 110 communicates with central nozzle chamber 170 through a plurality of gas transfer ports 192 formed in the internal wall 135 of housing 50. The gas transfer ports 192 permit spent gas from the nozzle assembly 180 to return to the pump 20 for repressurization and circulation, as explained in more detail below. This is caused by suction created by pump 20.

Referring once again to FIG. 5, the housing 50 of the gas conditioning unit 30 also includes a diverter plate 210 which interacts with the outlet cover 90 to define, among other features, a conditioning cavity 212 therebetween. The conditioning cavity 212 forms part of the second internal flow path, communicates with outlet port 94 in end cap 90, and is configured to support a planar filter element 220 made from a non-woven mesh or the like for filtering insufflation gas delivered from the gas source 18. Diverter plate 210 also includes a central aperture 215 to accommodate the passage of breathing tube 165.

Figure 10:
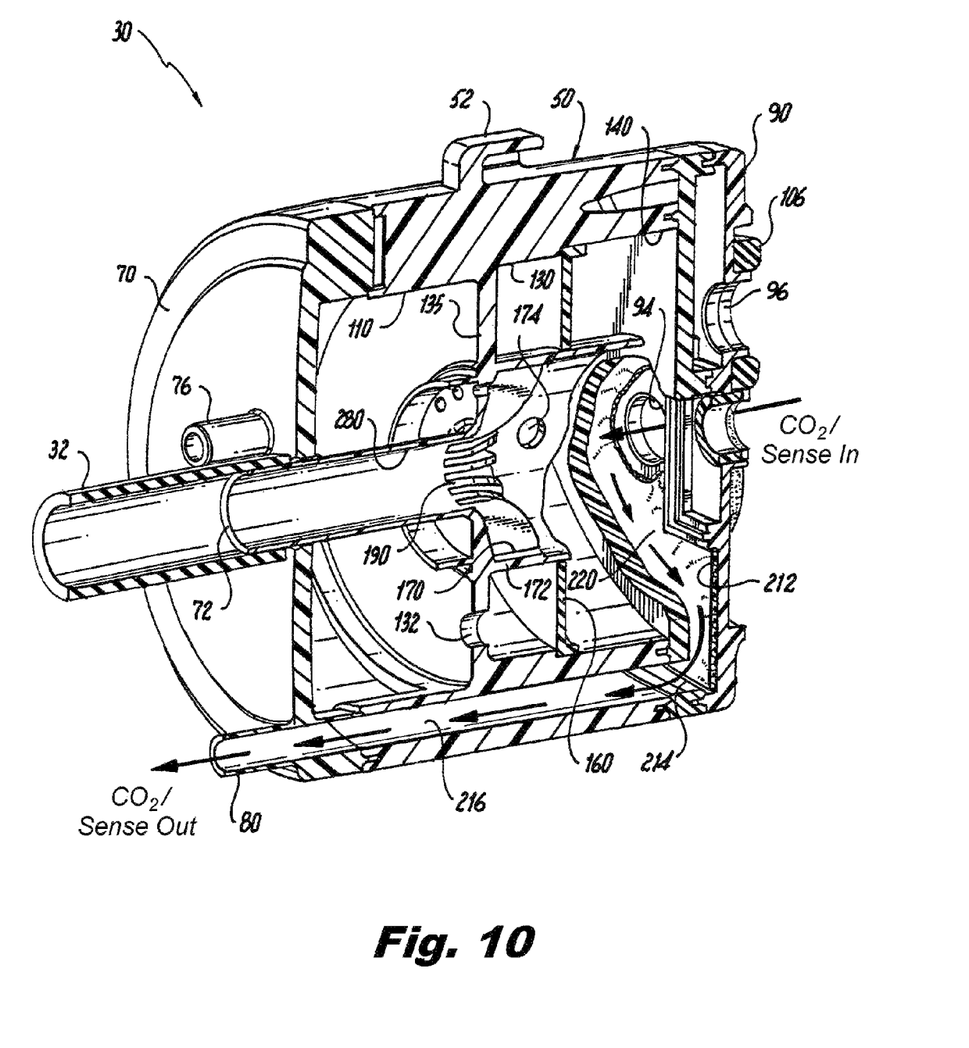
FIG. 10 is a cross-sectional view of the gas conditioning unit of the subject invention with a wall broken away to illustrate the insufflation/sensing path layout within the housing of the unit.

Referring now to FIG. 10, during operation, insufflation gas is delivered from the gas source 18 into the conditioning cavity 212 through the inlet port 94 in the rear end cap 90. The gas is conditioned or otherwise filtered as it passes through planar filter element 220. The filtered gas exists the conditioning cavity 212 through the crescent shaped side aperture 214 in diverter plate 210 and then flows into the internal side flow passage 216 of housing 50. The insufflating gas then exits from the housing 50 by way of conduit tube 80 in the front end cap 70 for delivery to the patient 15 through flexible conduit 36.

This same pathway shown in FIG. 10 is used to periodically sense abdominal pressure. That is, the flow of insufflation gas from gas source 18 is intermittently turned off by a valve (not shown) located in the housing 14 of gas delivery device 12. As a result, there are intervals of time in which there is no flow through the sensing path (e.g. through path 216 in housing 50). At such times, static pressure within the abdominal cavity can be measured by the gas delivery device 12 by way of conduit 36. This pressure measurement is utilized to adjust the flow of gas to the abdominal cavity, for example.

Referring now to FIG. 11, during operation, pressurized gas is delivered from the pump 20 in gas delivery device 12 through the inlet port 92 in the rear end cap 90. The pressurized gas then passes through the centrally offset circular aperture 218 in diverter plate 210 and then into the pressure chamber 140, where it is conditioned or otherwise filtered by passing through pleated filter element 150.

The pressurized gas then travels to the central nozzle chamber 170 by way of internal delivery port 174. In the central nozzle chamber 170, the pressurized gas is directed through the nozzle assembly 180 where it forms a pressure barrier within the upper region of central tubular passage 280 that is operatively associated with the conduit tube 72, as best seen in FIG. 12. This pressure barrier or working zone prohibits the egress of insufflation gas coming up from the abdominal cavity through flexible conduit 32 and conduit tube 72, while maintaining a stable pneumoperitoneum within the abdominal cavity of the patient 15.

Figure 13:
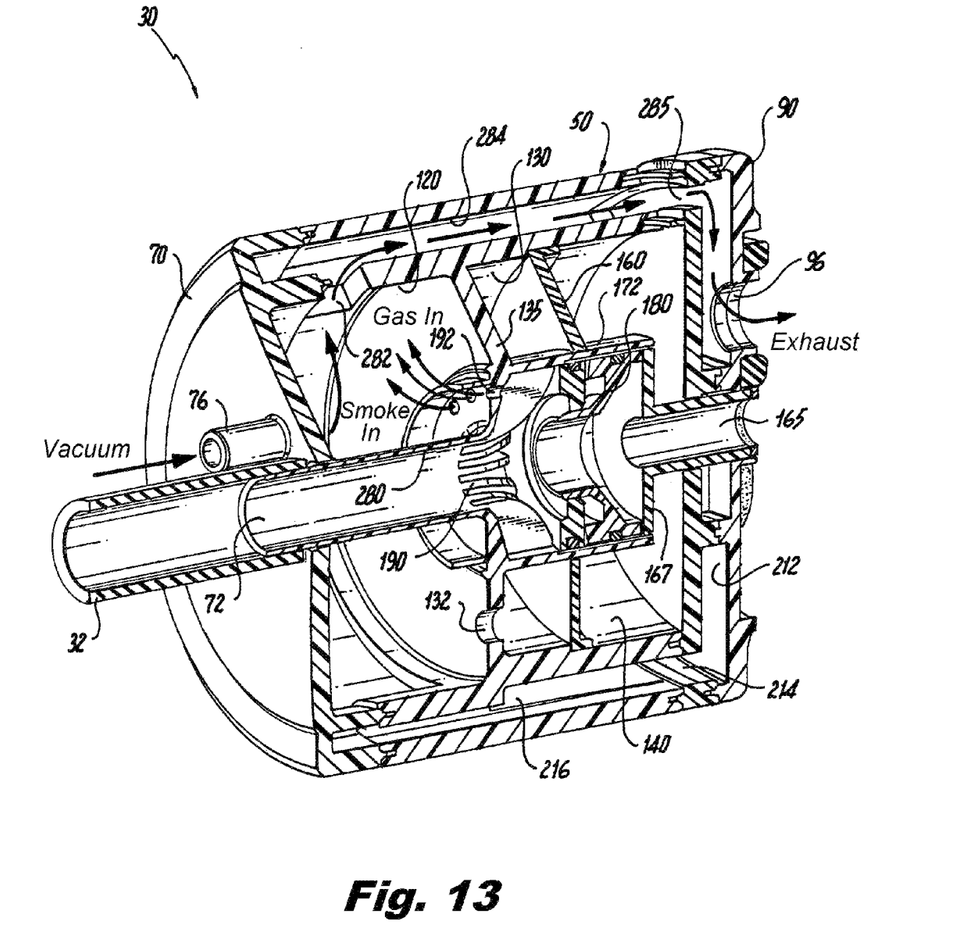
FIG. 13 is a cross-sectional view of the gas conditioning unit of the subject invention with a wall broken away to illustrate the vacuum path layout within the housing.

Referring to FIG. 13, during operation, gas from the abdominal cavity of the patient is drawn into the housing 50 through conduit connection 76 of end cap 70 under the suction created by pump 20. The gas that is drawn into the housing 50 may include bodily fluids, smoke from cauterization procedures and/or other debris from the ongoing laparoscopic surgical procedure. That flow of fluid/gas/solids is filtered within the vacuum chamber 110 by pleated filter element 120. The filtered gas is drawn out of vacuum chamber 110 through the side port 282 and into the lateral flow path 284 formed in housing 50. That gas then flows through the crescent shaped side aperture 285 in diverter plate 210 and out of the housing 50 through exit port 96 in the rear end cap 90.

The suction from pump assembly 20 also draws the spent fluid/gas that had been used to develop the pressure barrier within the conditioning unit through the plural apertures 192 formed in the floor of the nozzle chamber 170. That spent fluid/gas enters into the vacuum chamber 110, flows through the side port 282 and into the lateral flow path 284. The spent fluid/gas along with the filtered gas from the abdomen exits the housing 50 through exit port 96 and returns to pump 20. The conditioned flow is repressurized by the pump 20 and recirculated back to the housing 50 through pressure aperture 92 for subsequent delivery to the nozzle assembly 180 in nozzle chamber 170.

Figure 14:
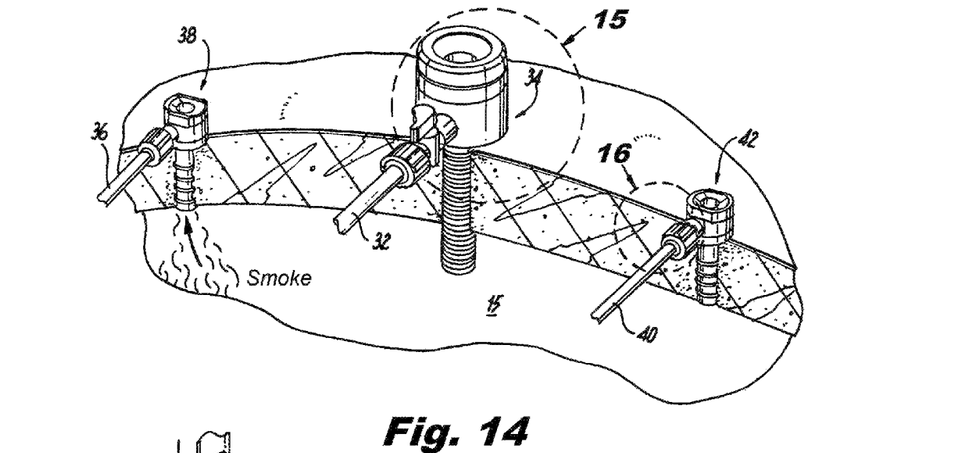
FIG. 14 illustrates the manner in which the flexible conduits associated with the gas conditioning unit are connected to respective surgical access devices communicating directly with the abdominal cavity of a patient, which includes a conventional valved trocar for instrument access, a cannula for vacuum return associated with smoke evacuation and another cannula for insufflation and sensing.
Figures 15, 16:
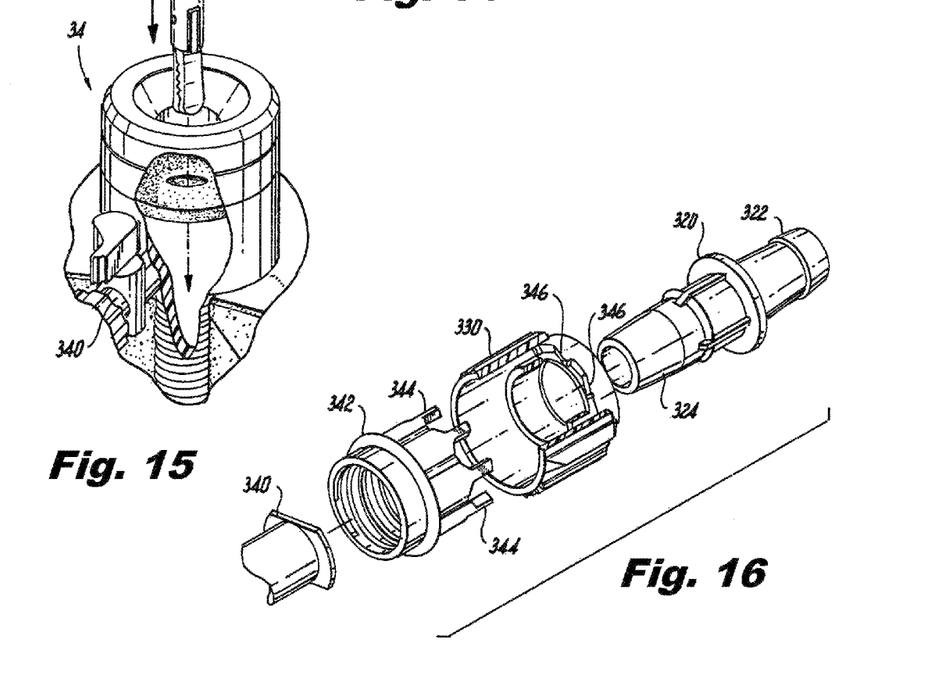
FIG. 15 is an enlarged localized perspective view of the conventional valved cannula shown in FIG. 14.
FIG. 16 is an exploded perspective view of the components of the coupling used to connect the pressurized gas supply conduit to the conventional trocar shown in FIG. 13.

Referring now to FIGS. 14 through 16, as discussed above, the flexible conduits associated with the gas conditioning unit 30 are respectively connected to separate surgical access devices communicating directly with the abdominal cavity of a patient. These devices include a conventional valved trocar for enabling instrument access 34, as shown in FIG. 15. That is, trocar 34 includes a mechanical valve such as a duckbill valve or the like designed to mechanically inhibit the egress of insufflating gas from the abdominal cavity by way of the access port, in combination with the pressure barrier or working zone formed within conditioning unit 30 by nozzle assembly 180. The access devices further include a first conventional cannula 38 for vacuum return associated with smoke evacuation procedures, and a second conventional cannula 42 for facilitating insufflation of and static pressure sensing from the abdominal cavity 15.

Because a conventional trocar includes a standard leur-type fitting 340, an adapter assembly 300 is provided to connect the large diameter conduit 32 to the fitting 340 of the trocar 34. The adapter assembly 300 includes a single lumen tubing connector 320 having a first end 322 dimensioned and configured to receive the large diameter conduit 32 and a second end 324 of reduced sized for communicating with the trocar 34.

The tubing connector 320 is supported within a rotatable gripping collar 330, and the gripping collar 330 interfits with a threaded member 342. The threaded member 342 connects directly with the leur fitting 340 on trocar 34. The threaded member 342 includes a plurality of rearward facing ratchet fingers 344 for interacting with a series of stepped ratchet pawls 346 formed within the interior of the gripping collar 330. This interaction allows for a specific torque to be applied to the collar 330 when connecting the conduit 32 to trocar 34. A similar mechanism is disclosed in commonly assigned U.S. patent Application publication 2014/0171855, the disclosure of which is herein incorporated by reference in its entirety.

While the gas delivery device and associated gas conditioning unit of the subject invention have been shown and described with reference to a preferred embodiment, those skilled in the art will readily appreciate that various changes and/or modifications may be made thereto without departing from the spirit and scope of the subject invention as defined by the appended claims. For example, the locations and relative positions of each of the gas flow paths formed within the conditioning unit could vary, and the type and size of the filter elements used within the conditioning unit could also vary.

What is claimed is:

1. A system for delivering gas during a laparoscopic surgical procedure performed within a patient's abdominal cavity, comprising:
   a) a gas delivery device having a housing with a port for receiving insufflating gas from a gas source, the housing of the gas delivery device being configured for enclosing a pump for circulating pressurized gas throughout the system;
   b) a separate gas conditioning unit having a housing configured for operative association with the gas delivery device and including:
      i) a first internal flow path for receiving pressurized gas delivered from the pump;
      ii) a second internal flow path for delivering insufflating gas to the abdominal cavity and for facilitating periodic static pressure measurements from the abdominal cavity; and
      iii) a third internal flow path for returning pressurized gas to the pump; and
   wherein the first internal flow path includes an internal nozzle assembly that is located within the housing of the gas conditioning unit and is configured to accelerate the pressurized gas delivered by the pump enclosed in the gas delivery device to the gas conditioning unit and thereby generate a continuous pressure barrier contained within the gas conditioning unit that inhibits egress of insufflating gas from the abdominal cavity, wherein the housing of the gas conditioning unit is generally cylindrical and includes an inlet end and an opposed outlet end, and wherein the gas delivery unit includes an engagement port for detachably receiving the gas conditioning unit, wherein the outlet end of the housing of the gas conditioning unit includes an outlet cover having a first outlet port corresponding to the first internal flow path, a second outlet port corresponding to the second internal flow path and a third outlet port corresponding to the third internal flow path.

2. A system as recited in claim 1, wherein the inlet end of the gas conditioning unit includes an inlet cover having a first inlet port corresponding to the first internal flow path which communicates with a first conduit, a second inlet port corresponding to the second internal flow path which communicates with a second conduit and a third inlet port corresponding to the third internal flow path which communicates with a third conduit.

3. A system as recited in claim 2, wherein the first conduit includes a fitting for communicating with a first surgical access port, and wherein the first surgical access port includes a mechanical valve associated with a central lumen thereof for accommodating the sealed introduction of surgical instruments into the abdominal cavity.

4. A system as recited in claim 2, wherein the second conduit includes a fitting for communicating with a second surgical access port responsible for insufflation and pressure measurement of the abdominal cavity.

5. A system as recited in claim 2, wherein the third conduit includes a fitting for communicating with a third surgical access port responsible for smoke evacuation from the abdominal cavity.

6. A system as recited in claim 1, wherein the housing of the gas conditioning unit includes an internal pressure chamber located within the first internal flow path and communicating with the first outlet port.

7. A system as recited in claim 6, wherein the housing of the gas conditioning unit includes an internal central nozzle chamber having a cylindrical wall supporting the internal nozzle assembly, and wherein the internal central nozzle chamber communicates with the internal pressure chamber through an internal delivery port.

8. A system as recited in claim 7, wherein the internal nozzle assembly includes a cylindrical jet set having a pair of axially spaced apart outer sealing rings for sealingly isolating the internal nozzle assembly within the central nozzle chamber.

9. A system as recited in claim 8, wherein the internal central nozzle chamber includes a plurality of circumferentially disposed spaced apart axial vanes distal to the cylindrical jet set for directing gas flow.

10. A system as recited in claim 8, wherein the internal central nozzle chamber communicates with a breathing tube proximal to the cylindrical jet set that is open to atmosphere.

11. A system as recited in claim 7, wherein the housing of the gas conditioning unit includes an internal vacuum chamber located within the third internal flow path.

12. A system as recited in claim 11, wherein the internal vacuum chamber communicates with the internal nozzle chamber through a plurality of gas transfer ports to permit spent gas from the internal nozzle assembly to return to the pump for repressurization and circulation.

13. A system as recited in claim 11, wherein a third filter element is disposed within the internal vacuum chamber for filtering gas returning to the pump from the patient's abdominal cavity.

14. A system as recited in claim 11, wherein the housing of the gas conditioning unit further includes an internal reservoir chamber located within the third internal flow path, downstream from and in fluid communication with the internal vacuum chamber through a fluid transfer port, for accommodating any fluid drawn into the housing of the gas conditioning unit by the pump.

15. A system as recited in claim 14, wherein a fluid level sensor is arranged within the internal reservoir for detecting a predetermined fluid level therein.

16. A system as recited in claim 6, wherein a first filter element is disposed within the internal pressure chamber for filtering pressurized gas from the pump.

17. A system as recited in claim 1, wherein the housing of the gas conditioning unit includes a diverter plate which interacts with the outlet cover to define an internal conditioning cavity disposed in the second internal flow path and configured to support a second filter element for filtering insufflating gas from the gas source.

18. A gas conditioning unit for use with a gas delivery device during a laparoscopic surgical procedure performed within a patient's abdominal cavity, comprising:
   a) a housing having an inlet end configured for engagement with the gas delivery device and an opposed outlet end;
   b) a first filtered flow path within the housing for receiving pressurized gas from a pump enclosed within the gas delivery device;
   c) a second filtered flow path within the housing for delivering insufflating gas to the abdominal cavity and for facilitating periodic static pressure measurements from the abdominal cavity; and
   d) a third filtered flow path for returning pressurized gas to the pump;
   wherein the first filtered flow path includes an internal annular nozzle assembly that is located within the housing of the gas conditioning unit and is dimensioned and configured to accelerate the pressurized gas delivered by the pump and thereby generate a continuous pressure barrier contained within the gas conditioning unit that inhibits egress of insufflating gas from the abdominal cavity, and wherein the outlet end of the housing of the gas conditioning unit includes an outlet cover having a first outlet port corresponding to the first filtered flow path, a second outlet port corresponding to the second filtered flow path and a third outlet port corresponding to the third filtered flow path.

19. A gas conditioning unit as recited in claim 18, wherein the inlet end of the gas conditioning unit includes an inlet cover having a first inlet port corresponding to the first filtered flow path which communicates with a first conduit, a second inlet port corresponding to the second filtered flow path which communicates with a second conduit and a third inlet port corresponding to the third filtered flow path which communicates with a third conduit.

20. A gas conditioning unit as recited in claim 19, wherein the first conduit includes a fitting for communicating with a first surgical access port, and wherein the first surgical access port includes a mechanical valve associated with a central lumen thereof for accommodating the introduction of surgical instruments into the abdominal cavity.

21. A gas conditioning unit as recited in claim 18, wherein the housing of the gas conditioning unit includes an internal pressure chamber located within the first flow path and communicating with the first outlet port.

22. A gas conditioning unit as recited in claim 21, wherein a first filter element is disposed within the internal pressure chamber for filtering pressurized gas from the pump.

23. A gas conditioning unit as recited in claim 18, wherein the housing of the gas conditioning unit includes an internal central nozzle chamber having a cylindrical wall supporting the internal annular nozzle assembly, and wherein the internal central nozzle chamber communicates with the internal pressure chamber through an internal delivery port.

24. A gas conditioning unit as recited in claim 23, wherein the internal annular nozzle assembly includes a cylindrical jet set having a pair of axially spaced apart outer sealing rings for sealingly isolating the internal nozzle assembly within the internal central nozzle chamber.

25. A gas conditioning unit as recited in claim 23, wherein the internal central nozzle chamber includes a plurality of circumferentially disposed spaced apart axial fins distal to the cylindrical jet set for directing gas flow.

26. A gas conditioning unit as recited in claim 23, wherein the internal central nozzle chamber communicates with a breathing tube proximal to the cylindrical jet set that is open to atmosphere.

27. A gas conditioning unit as recited in claim 23, wherein the housing of the gas conditioning unit includes an internal vacuum chamber located within the third filtered gas path.

28. A gas conditioning unit as recited in claim 27, wherein the internal vacuum chamber communicates with the internal nozzle chamber through a plurality of gas transfer ports to permit spent gas from the internal nozzle assembly to return to the pump for repressurization and circulation.

29. A gas conditioning unit as recited in claim 28, wherein a third filter element is disposed within the internal vacuum chamber for filtering gas returning to the pump from the patient's abdominal cavity.

30. A gas conditioning unit as recited in claim 29, wherein the housing of the gas conditioning unit further includes an internal reservoir chamber located within the third filtered flow path, downstream from and in fluid communication with the internal vacuum chamber through a fluid transfer port, for accommodating any fluid drawn into the housing of the gas conditioning unit by the pump.

31. A gas conditioning unit as recited in claim 30, wherein a fluid level sensor is arranged within the internal reservoir for detecting a predetermined fluid level therein.

32. A gas conditioning unit as recited in claim 18, wherein the housing of the gas conditioning unit includes a diverter plate which interacts with the outlet cover to define an internal conditioning cavity disposed in the second filtered flow path and configured to support a second filter element for filtering insufflation gas from the gas source.

33. A gas conditioning unit as recited in claim 18, wherein the second conduit includes a fitting for communicating with a second surgical access port responsible for insufflation and pressure measurement of the abdominal cavity.

34. A gas conditioning unit as recited in claim 18, wherein the third conduit includes a fitting for communicating with a third surgical access port responsible for smoke evacuation from the abdominal cavity.

* * * * *